(12) United States Patent  (10) Patent No.: US 8,394,981 B2
Garner et al.  (45) Date of Patent: *Mar. 12, 2013

(54) HYDROCYANATION OF 2-PENTENENITRILE

(75) Inventors: James Michael Garner, Wilmington, DE (US); Christian P. Lenges, Wilmington, DE (US); Ronald J. McKinney, Wilmington, DE (US); Wilson Tam, Boothwyn, PA (US)

(73) Assignee: Invista North America S.A R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/022,208

(22) Filed: Feb. 7, 2011

(65) Prior Publication Data

US 2012/0035387 A1   Feb. 9, 2012

Related U.S. Application Data

(62) Division of application No. 11/776,904, filed on Jul. 12, 2007, now Pat. No. 7,919,646.

(51) Int. Cl.
  *C07C 253/00* (2006.01)
(52) U.S. Cl. ...................................................... 558/338
(58) Field of Classification Search ................... 558/338
  See application file for complete search history.

(56) References Cited

U.S. PATENT DOCUMENTS

| | | | |
|---|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard, Jr. et al. |
| 3,551,474 A | 12/1970 | Drinkard et al. |
| 3,564,040 A | 2/1971 | Downing et al. |
| 3,579,560 A | 5/1971 | Drinkard et al. |
| 3,631,191 A | 12/1971 | Kane et al. |
| 3,655,723 A | 4/1972 | Drinkard, Jr. et al. |
| 3,676,481 A | 7/1972 | Chia |
| 3,694,485 A | 9/1972 | Drinkard, Jr. et al. |

(Continued)

FOREIGN PATENT DOCUMENTS

| | | |
|---|---|---|
| AU | 6522096 | 2/1997 |
| AU | 199665220 A | 2/1997 |

(Continued)

OTHER PUBLICATIONS

Tolman et al., Advances in Catalysis, 1985, 33, pp. 1-46.

*Primary Examiner* — Rei-tsang Shiao

(57) ABSTRACT

The invention provides a process for hydrocyanation, comprising: contacting 2-pentenenitrile with hydrogen cyanide at a temperature in the range of about 0° C. to about 150° C. in the presence of at least one Lewis acid promoter and a catalyst precursor composition, wherein the catalyst precursor composition comprises a zero-valent nickel and at least one bidentate phosphite ligand selected from a member of the group represented by Formula I and Formula II, in which all like reference characters have the same meaning, except as further explicitly limited:

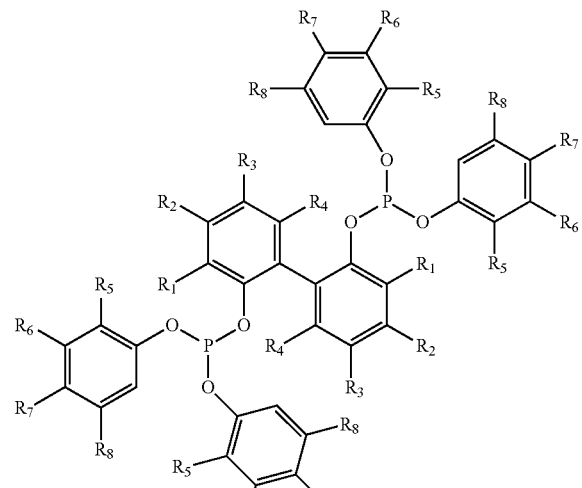

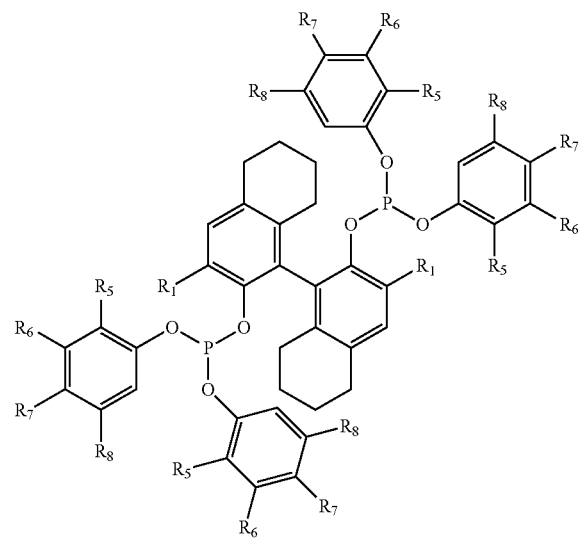

wherein $R_1$ and $R_5$ are independently selected from the group consisting of $C_1$ to $C_5$ hydrocarbyl; and $R_2$, $R_3$, $R_4$, $R_6$, $R_7$ and $R_8$ are independently selected from the group consisting of H and $C_1$ to $C_4$ hydrocarbyl.

8 Claims, No Drawings

U.S. PATENT DOCUMENTS

| | | | |
|---|---|---|---|
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,852,325 A | 12/1974 | King |
| 3,852,327 A | 12/1974 | Druliner et al. |
| 3,853,754 A | 12/1974 | Gosser |
| 3,853,948 A | 12/1974 | Drinkard, Jr. et al. |
| 3,864,380 A | 2/1975 | King et al. |
| 3,865,865 A | 2/1975 | Musser et al. |
| 3,869,501 A | 3/1975 | Waddan |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,328,172 A | 5/1982 | Rapoport |
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |
| 4,416,825 A | 11/1983 | Ostermaier |
| 4,434,316 A | 2/1984 | Barnette |
| 4,539,302 A | 9/1985 | Leyendecker et al. |
| 4,705,881 A | 11/1987 | Rapoport |
| 4,749,801 A | 6/1988 | Beatty et al. |
| 4,774,353 A | 9/1988 | Hall et al. |
| 4,874,884 A | 10/1989 | McKinney et al. |
| 4,990,645 A | 2/1991 | Back et al. |
| 5,107,012 A | 4/1992 | Grunewald |
| 5,302,756 A | 4/1994 | McKinney |
| 5,312,959 A | 5/1994 | Sieja et al. |
| 5,449,807 A | 9/1995 | Druliner |
| 5,488,129 A | 1/1996 | Huser et al. |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,696,280 A | 12/1997 | Shapiro |
| 5,709,841 A | 1/1998 | Reimer |
| 5,723,641 A | 3/1998 | Tam et al. |
| 5,773,637 A | 6/1998 | Cicha et al. |
| 5,821,378 A | 10/1998 | Foo et al. |
| 5,847,191 A | 12/1998 | Bunel et al. |
| 5,856,555 A | 1/1999 | Huser et al. |
| 5,908,805 A | 6/1999 | Huser et al. |
| 5,959,135 A | 9/1999 | Garner et al. |
| 5,981,772 A | 11/1999 | Foo et al. |
| 6,020,516 A | 2/2000 | Foo et al. |
| 6,069,267 A | 5/2000 | Tam |
| 6,090,987 A | 7/2000 | Billig et al. |
| 6,121,184 A | 9/2000 | Druliner et al. |
| 6,127,567 A | 10/2000 | Garner et al. |
| 6,147,247 A | 11/2000 | Voit et al. |
| 6,169,198 B1 | 1/2001 | Fischer et al. |
| 6,171,996 B1 | 1/2001 | Garner et al. |
| 6,197,992 B1 | 3/2001 | Fischer et al. |
| 6,242,633 B1 | 6/2001 | Fischer et al. |
| 6,284,865 B1 | 9/2001 | Tam et al. |
| 6,307,109 B1 | 10/2001 | Kanel et al. |
| 6,355,833 B2 | 3/2002 | Fischer et al. |
| 6,461,481 B1 | 10/2002 | Barnette et al. |
| 6,469,194 B2 | 10/2002 | Burattin et al. |
| 6,521,778 B1 | 2/2003 | Fischer et al. |
| 6,646,148 B1 | 11/2003 | Kreutzer |
| 6,660,877 B2 | 12/2003 | Lenges et al. |
| 6,737,539 B2 | 5/2004 | Lenges et al. |
| 6,753,440 B2 | 6/2004 | Druliner et al. |
| 6,770,770 B1 | 8/2004 | Baumann et al. |
| 6,846,945 B2 | 1/2005 | Lenges et al. |
| 6,852,199 B2 | 2/2005 | Jungkamp et al. |
| 6,855,799 B2 | 2/2005 | Tam et al. |
| 6,893,996 B2 | 5/2005 | Chu et al. |
| 6,897,329 B2 | 5/2005 | Jackson et al. |
| 6,969,267 B2 | 11/2005 | Byquist |
| 6,984,604 B2 | 1/2006 | Cobb et al. |
| 7,022,866 B2 | 4/2006 | Bartsch et al. |
| 7,067,685 B2 | 6/2006 | Bartsch et al. |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,700,795 B2 | 4/2010 | Haderlein et al. |
| 7,919,646 B2 * | 4/2011 | Garner et al. ............... 558/338 |
| 2003/0135014 A1 | 7/2003 | Radu et al. |
| 2003/0212298 A1 | 11/2003 | Brasse et al. |
| 2004/0063991 A1 | 4/2004 | Burattin et al. |
| 2004/0106815 A1 | 6/2004 | Ritter |
| 2004/0176622 A1 | 9/2004 | Bartsch et al. |
| 2004/0235648 A1 | 11/2004 | Bartsch et al. |
| 2004/0260112 A1 | 12/2004 | Basset et al. |
| 2005/0090677 A1 | 4/2005 | Bartsch et al. |
| 2005/0090678 A1 | 4/2005 | Bartsch et al. |
| 2005/0247624 A1 | 11/2005 | Jungkamp et al. |
| 2006/0142609 A1 | 6/2006 | Bourgeois et al. |
| 2006/0175189 A1 | 8/2006 | Gerber et al. |
| 2006/0252955 A1 | 11/2006 | Rosier et al. |
| 2006/0258873 A1 | 11/2006 | Rosier et al. |
| 2006/0258874 A1 | 11/2006 | Bartsch et al. |
| 2006/0264651 A1 | 11/2006 | Bartsch et al. |
| 2007/0060766 A1 | 3/2007 | Bartsch et al. |
| 2007/0073071 A1 | 3/2007 | Haderlein et al. |
| 2007/0083057 A1 | 4/2007 | Haderlein et al. |
| 2007/0088173 A1 | 4/2007 | Haderlein et al. |
| 2007/0112215 A1 | 5/2007 | Jungkamp et al. |
| 2007/0155977 A1 | 7/2007 | Jungkamp et al. |
| 2007/0155978 A1 | 7/2007 | Jungkamp et al. |
| 2007/0155980 A1 | 7/2007 | Scheidel et al. |
| 2008/0015378 A1 | 1/2008 | Foo et al. |
| 2008/0015380 A1 | 1/2008 | Foo et al. |
| 2008/0015381 A1 | 1/2008 | Foo et al. |
| 2008/0015382 A1 | 1/2008 | Foo et al. |
| 2008/0071105 A1 | 3/2008 | Bartsch et al. |
| 2008/0076944 A1 | 3/2008 | Bartsch et al. |
| 2008/0083607 A1 | 4/2008 | Deckert et al. |
| 2008/0221351 A1 | 9/2008 | Bartsch et al. |
| 2008/0227214 A1 | 9/2008 | Jungkamp et al. |
| 2008/0227998 A1 | 9/2008 | Scheidel et al. |
| 2008/0242883 A1 | 10/2008 | Jungkamp et al. |
| 2008/0242885 A1 | 10/2008 | Jungkamp et al. |
| 2008/0242886 A1 | 10/2008 | Bartsch et al. |
| 2008/0275266 A1 | 11/2008 | Bartsch et al. |
| 2008/0281119 A1 | 11/2008 | Scheidel et al. |
| 2008/0281120 A1 | 11/2008 | Jungkamp et al. |
| 2009/0054671 A1 | 2/2009 | Haderlein et al. |

FOREIGN PATENT DOCUMENTS

| | | |
|---|---|---|
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |
| CN | 1535179 A | 10/2004 |
| CN | 1564807 A | 1/2005 |
| CN | 1568225 A | 1/2005 |
| CN | 1568226 A | 1/2005 |
| CN | 1617892 A | 5/2005 |
| CN | 1617900 A | 5/2005 |
| CN | 1212293 C | 7/2005 |
| CN | 1639176 A | 7/2005 |
| CN | 1213051 C | 8/2005 |
| CN | 1665776 A | 9/2005 |
| CN | 1670139 A | 9/2005 |
| CN | 1674989 A | 9/2005 |
| CN | 1675172 A | 9/2005 |
| CN | 1222358 C | 10/2005 |
| CN | 1732148 A | 2/2006 |
| CN | 1735460 A | 2/2006 |
| CN | 1245489 C | 3/2006 |
| CN | 1740183 A | 3/2006 |
| CN | 1745062 A | 3/2006 |
| CN | 1767895 A | 5/2006 |
| CN | 1260009 C | 6/2006 |
| CN | 1266424 C | 7/2006 |
| CN | 1270543 C | 8/2006 |
| CN | 1274671 C | 9/2006 |
| CN | 1274699 C | 9/2006 |
| CN | 1835915 A | 9/2006 |
| CN | 1279088 C | 10/2006 |
| CN | 1837288 A | 10/2006 |
| CN | 1283620 C | 11/2006 |
| CN | 1857775 A | 11/2006 |
| CN | 1289539 C | 12/2006 |
| CN | 1293942 C | 1/2007 |
| CN | 1906150 A | 1/2007 |
| CN | 1914154 A | 2/2007 |
| CN | 1914155 A | 2/2007 |
| CN | 1914156 A | 2/2007 |
| CN | 1914157 A | 2/2007 |
| CN | 1914158 A | 2/2007 |
| CN | 1914159 A | 2/2007 |
| CN | 1914160 A | 2/2007 |
| CN | 1914161 A | 2/2007 |
| CN | 1914162 A | 2/2007 |
| CN | 1914165 A | 2/2007 |
| CN | 1914166 A | 2/2007 |
| CN | 1914167 A | 2/2007 |
| CN | 1914216 A | 2/2007 |
| CN | 1307237 C | 3/2007 |
| CN | 1315790 C | 5/2007 |
| CN | 1318432 C | 5/2007 |
| CN | 1997624 A | 7/2007 |
| CN | 1331843 C | 8/2007 |
| CN | 101020641 A | 8/2007 |
| CN | 101035799 A | 9/2007 |
| CN | 101043946 A | 9/2007 |
| CN | 100348322 C | 11/2007 |
| CN | 100351227 C | 11/2007 |
| CN | 100352824 C | 12/2007 |
| CN | 100361966 C | 1/2008 |
| CN | 1000364666 C | 1/2008 |
| DE | 1807088 U | 3/1960 |
| DE | 1807088 A1 | 6/1969 |
| DE | 2055747 A1 | 5/1971 |
| DE | 1593277 B2 | 8/1973 |
| DE | 1593277 C3 | 3/1974 |
| DE | 2700904 C2 | 10/1983 |
| DE | 68909466 T2 | 3/1994 |
| DE | 10136488 A1 | 2/2003 |
| DE | 10150285 A1 | 4/2003 |
| DE | 10350999 A1 | 6/2005 |
| DE | 102004004696 A1 | 8/2005 |
| EP | 0001899 B1 | 3/1982 |
| EP | 123438 B1 | 7/1987 |
| EP | 160296 B1 | 10/1988 |
| EP | 268448 B1 | 9/1991 |
| EP | 510689 A1 | 10/1992 |
| EP | 248643 B1 | 3/1993 |
| EP | 336314 B1 | 9/1993 |
| EP | 464691 B1 | 12/1993 |
| EP | 675871 B1 | 4/1997 |
| EP | 634395 B1 | 9/1997 |
| EP | 650959 B1 | 9/1997 |
| EP | 784610 B1 | 2/1999 |
| EP | 757672 B1 | 6/1999 |
| EP | 792259 B1 | 8/1999 |
| EP | 804412 B1 | 12/1999 |
| EP | 1000019 A1 | 5/2000 |
| EP | 1001928 A1 | 5/2000 |
| EP | 1003716 A1 | 5/2000 |
| EP | 1019190 A1 | 7/2000 |
| EP | 755302 B1 | 10/2000 |
| EP | 929513 B1 | 4/2001 |
| EP | 881924 B1 | 5/2001 |
| EP | 854858 B1 | 6/2001 |
| EP | 815073 B1 | 7/2001 |
| EP | 1144114 A3 | 9/2001 |
| EP | 1091804 B1 | 2/2002 |
| EP | 944585 B1 | 4/2002 |
| EP | 1000019 B1 | 2/2003 |
| EP | 911339 B1 | 4/2003 |
| EP | 1216268 B1 | 11/2003 |
| EP | 1350788 A3 | 11/2003 |
| EP | 1003607 B1 | 12/2003 |
| EP | 1003716 B1 | 2/2004 |
| EP | 1313743 B1 | 3/2004 |
| EP | 1414567 A1 | 5/2004 |

| | | | | | | |
|---|---|---|---|---|---|---|
| EP | 1427695 | A1 | 6/2004 | JP | 52012698 B | 4/1977 |
| EP | 1438133 | A1 | 7/2004 | JP | 1013127 C | 9/1980 |
| EP | 1019190 | B1 | 12/2004 | JP | 55047031 B | 11/1980 |
| EP | 1140801 | B1 | 2/2005 | JP | 57156454 U | 10/1982 |
| EP | 1395547 | B1 | 3/2005 | JP | 57156455 U | 10/1982 |
| EP | 1001928 | B1 | 4/2005 | JP | 57179144 U | 11/1982 |
| EP | 1521736 | A1 | 4/2005 | JP | 1136333 C | 2/1983 |
| EP | 1521737 | A1 | 4/2005 | JP | 58067658 U | 5/1983 |
| EP | 1521738 | A2 | 4/2005 | JP | 58126892 U | 8/1983 |
| EP | 1603865 | A1 | 12/2005 | JP | 1170710 C | 10/1983 |
| EP | 1324976 | B1 | 2/2006 | JP | 58159452 U | 10/1983 |
| EP | 1214975 | B1 | 3/2006 | JP | 60044295 A | 3/1985 |
| EP | 1324978 | B1 | 3/2006 | JP | 60044295 B | 10/1985 |
| EP | 1648860 | A1 | 4/2006 | JP | 62294691 A | 12/1987 |
| EP | 891323 | B1 | 6/2006 | JP | 63135363 U | 9/1988 |
| EP | 1226147 | B1 | 6/2006 | JP | 1013127 Y2 | 4/1989 |
| EP | 1438317 | B1 | 6/2006 | JP | 1209830 A | 8/1989 |
| EP | 1682561 | A1 | 7/2006 | JP | 1136333 U | 9/1989 |
| EP | 1448668 | B1 | 8/2006 | JP | 1050220 B | 10/1989 |
| EP | 1587621 | B1 | 8/2006 | JP | 1173751 U | 12/1989 |
| EP | 1713759 | A1 | 10/2006 | JP | 1565159 C | 6/1990 |
| EP | 1713761 | A1 | 10/2006 | JP | 3001298 B | 1/1991 |
| EP | 1713762 | A1 | 10/2006 | JP | 1615749 C | 8/1991 |
| EP | 1713766 | A1 | 10/2006 | JP | 3205587 A | 9/1991 |
| EP | 1616109 | A2 | 11/2006 | JP | 1627124 C | 11/1991 |
| EP | 1716102 | A2 | 11/2006 | JP | 1627146 C | 11/1991 |
| EP | 1716103 | A1 | 11/2006 | JP | 3069915 B | 11/1991 |
| EP | 1716104 | A1 | 11/2006 | JP | 3285878 A | 12/1991 |
| EP | 1716105 | A1 | 11/2006 | JP | 1642102 C | 2/1992 |
| EP | 1716106 | A1 | 11/2006 | JP | 4012248 Y2 | 3/1992 |
| EP | 1716107 | A1 | 11/2006 | JP | 4057050 U | 5/1992 |
| EP | 1610893 | B1 | 3/2007 | JP | 4166155 A | 6/1992 |
| EP | 1621531 | B1 | 3/2007 | JP | 4230254 A | 8/1992 |
| EP | 1438132 | B1 | 4/2007 | JP | 4057050 B | 9/1992 |
| EP | 1799697 | A1 | 6/2007 | JP | 4060532 B | 9/1992 |
| EP | 1713764 | B1 | 8/2007 | JP | 4118676 U | 10/1992 |
| EP | 1713816 | B1 | 8/2007 | JP | 4128141 U | 11/1992 |
| EP | 1825914 | A1 | 8/2007 | JP | 1729140 C | 1/1993 |
| EP | 1448620 | B1 | 6/2008 | JP | 1811422 C | 12/1993 |
| EP | 1817108 | B1 | 6/2008 | JP | 7025841 Y2 | 6/1995 |
| EP | 1713760 | B1 | 7/2008 | JP | 7188144 A | 7/1995 |
| EP | 1571172 | B1 | 10/2008 | JP | 2037346 C | 3/1996 |
| EP | 1988998 | A1 | 11/2008 | JP | 8504814 A | 5/1996 |
| EP | 1265832 | B1 | 5/2009 | JP | 8157795 A | 6/1996 |
| EP | 1592659 | B1 | 7/2009 | JP | 2098106 C | 10/1996 |
| EP | 1586598 | B1 | 9/2009 | JP | 02521777 Y2 | 1/1997 |
| EP | 2098106 | A1 | 9/2009 | JP | 02623448 B2 | 6/1997 |
| EP | 1567478 | B1 | 10/2009 | JP | 9505586 A | 6/1997 |
| EP | 1682559 | B1 | 12/2009 | JP | 9512013 A | 12/1997 |
| EP | 1630166 | B1 | 2/2010 | JP | 10505101 A | 5/1998 |
| FR | 1544656 | A | 11/1968 | JP | 10506911 A | 7/1998 |
| FR | 2015115 | A5 | 4/1970 | JP | 10509954 A | 9/1998 |
| FR | 1603513 | A | 5/1971 | JP | 02818503 B2 | 10/1998 |
| FR | 2069411 | A5 | 9/1971 | JP | 10512879 A | 12/1998 |
| FR | 2845379 | B1 | 12/2004 | JP | 11501660 A | 2/1999 |
| FR | 2873696 | A1 | 2/2006 | JP | 11504262 A | 4/1999 |
| FR | 2873696 | B1 | 10/2006 | JP | 02911608 B2 | 6/1999 |
| GB | 0219474 | A | 7/1924 | JP | 11507297 A | 6/1999 |
| GB | 1104140 | A | 2/1968 | JP | 03001298 B2 | 1/2000 |
| GB | 1203702 | A | 9/1970 | JP | 03069915 B2 | 7/2000 |
| GB | 1213175 | A | 11/1970 | JP | 2001500135 A | 1/2001 |
| GB | 1429169 | A | 3/1976 | JP | 2001506250 A | 5/2001 |
| GB | 1429621 | A | 3/1976 | JP | 2001512097 A | 8/2001 |
| GB | 1436932 | A | 5/1976 | JP | 03205587 B2 | 9/2001 |
| GB | 1458322 | A | 12/1976 | JP | 2001516640 A | 10/2001 |
| GB | 1482909 | A | 8/1977 | JP | 03285878 B2 | 5/2002 |
| GB | 2007521 | A | 5/1979 | JP | 2002517473 A | 6/2002 |
| GB | 1565443 | A | 4/1980 | JP | 03320424 B2 | 9/2002 |
| GB | 1594694 | A | 8/1981 | JP | 2002533321 A | 10/2002 |
| GB | 2007521 | B | 6/1982 | JP | 03380543 B2 | 2/2003 |
| HK | 1025950 | A1 | 7/2003 | JP | 2003510385 A | 3/2003 |
| HK | 1026383 | A1 | 7/2004 | JP | 2003526688 A | 9/2003 |
| HK | 1052364 | A1 | 5/2007 | JP | 03478399 B2 | 12/2003 |
| JP | 48028423 | Y1 | 8/1973 | JP | 2004501058 A | 1/2004 |
| JP | 48028423 | B | 9/1973 | JP | 2004507550 A | 3/2004 |
| JP | 49043924 | Y1 | 12/1974 | JP | 03519410 B2 | 4/2004 |
| JP | 50058324 | U | 6/1975 | JP | 03535182 B2 | 6/2004 |
| JP | 50059326 | U | 6/1975 | JP | 03553952 B2 | 8/2004 |
| JP | 51007649 | B | 3/1976 | JP | 2004534032 A | 11/2004 |

| | | | | | | | |
|---|---|---|---|---|---|---|---|
| JP | 2004535929 | A | 12/2004 | WO | WO9528228 | A1 | 10/1995 |
| JP | 03621133 | B2 | 2/2005 | WO | WO9529153 | A1 | 11/1995 |
| JP | 2005503410 | A | 2/2005 | WO | WO9611182 | A1 | 4/1996 |
| JP | 2005505610 | A | 2/2005 | WO | WO9616022 | A1 | 5/1996 |
| JP | 2005505611 | A | 2/2005 | WO | WO9622968 | A1 | 8/1996 |
| JP | 2005510588 | A | 4/2005 | WO | WO9629303 | A1 | 9/1996 |
| JP | 2005510605 | A | 4/2005 | WO | WO9703040 | A1 | 1/1997 |
| JP | 2004509942X | | 10/2005 | WO | WO9712857 | A1 | 4/1997 |
| JP | 2005533095 | A | 11/2005 | WO | WO9724183 | A1 | 7/1997 |
| JP | 2005533096 | A | 11/2005 | WO | WO9736855 | A2 | 10/1997 |
| JP | 2005538075 | A | 12/2005 | WO | WO9811051 | A1 | 3/1998 |
| JP | 03739404 | B2 | 1/2006 | WO | WO9827054 | A1 | 6/1998 |
| JP | 2004534032X | | 1/2006 | WO | WO9906146 | A2 | 2/1999 |
| JP | 2004535929X | | 1/2006 | WO | WO9906356 | | 2/1999 |
| JP | 2005000451 | A | 1/2006 | WO | WO9906359 | A1 | 2/1999 |
| JP | 2006511591 | A | 4/2006 | WO | WO9913983 | A1 | 3/1999 |
| JP | 2006519797 | A | 8/2006 | WO | WO9964155 | A1 | 12/1999 |
| JP | 2006528616 | A | 12/2006 | WO | WO0001485 | A2 | 1/2000 |
| JP | 2007083057 | A | 4/2007 | WO | WO0037431 | A1 | 6/2000 |
| JP | 2007509885 | A | 4/2007 | WO | WO0121684 | A1 | 3/2001 |
| JP | 2007509886 | A | 4/2007 | WO | WO0136429 | A1 | 5/2001 |
| JP | 2007509887 | A | 4/2007 | WO | WO0168247 | A2 | 9/2001 |
| JP | 2007519516 | A | 7/2007 | WO | WO0213964 | A2 | 2/2002 |
| JP | 2007519663 | A | 7/2007 | WO | WO0222208 | A1 | 2/2002 |
| JP | 2007519664 | A | 7/2007 | WO | WO0218392 | | 3/2002 |
| JP | 2007519666 | A | 7/2007 | WO | WO0226698 | A1 | 4/2002 |
| JP | 2007519667 | A | 7/2007 | WO | WO0230854 | A2 | 4/2002 |
| JP | 2007519670 | A | 7/2007 | WO | WO02053527 | A1 | 7/2002 |
| JP | 2007519671 | A | 7/2007 | WO | WO02092551 | A2 | 11/2002 |
| JP | 2007519672 | A | 7/2007 | WO | WO03011457 | A1 | 2/2003 |
| JP | 2007519673 | A | 7/2007 | WO | WO03018540 | A1 | 3/2003 |
| JP | 2007519674 | A | 7/2007 | WO | WO03024919 | A1 | 3/2003 |
| JP | 2007519675 | A | 7/2007 | WO | WO03031392 | A1 | 4/2003 |
| JP | 2007519677 | A | 7/2007 | WO | WO03033141 | A1 | 4/2003 |
| JP | 2007522122 | A | 8/2007 | WO | WO03033509 | A1 | 4/2003 |
| JP | 04012248 | B2 | 11/2007 | WO | WO03046019 | A1 | 6/2003 |
| JP | 2006515323X | | 2/2008 | WO | WO03046049 | A1 | 6/2003 |
| JP | 04057050 | B2 | 3/2008 | WO | WO03068729 | A1 | 8/2003 |
| JP | 04060532 | B2 | 3/2008 | WO | WO03076394 | A1 | 9/2003 |
| JP | 2006512918X | | 3/2008 | WO | WO2004007431 | A1 | 1/2004 |
| JP | 2008515831 | A | 5/2008 | WO | WO2004007432 | A1 | 1/2004 |
| JP | 2008516907 | A | 5/2008 | WO | WO2004007435 | A2 | 1/2004 |
| JP | 04118676 | B2 | 7/2008 | WO | WO2004007508 | A2 | 1/2004 |
| JP | 04128141 | B2 | 7/2008 | WO | WO0168247 | A8 | 6/2004 |
| JP | 04166155 | B2 | 10/2008 | WO | WO2004060855 | A1 | 7/2004 |
| JP | 04230254 | B2 | 2/2009 | WO | WO2004064994 | A2 | 8/2004 |
| KR | 198802621 | Y1 | 7/1988 | WO | WO2004065352 | A2 | 8/2004 |
| KR | 198802296 | B1 | 10/1988 | WO | WO2004080924 | A2 | 9/2004 |
| KR | 198803396 | B | 10/1988 | WO | WO2004080948 | A1 | 9/2004 |
| KR | 199003458 | B1 | 5/1990 | WO | WO2004087314 | A1 | 10/2004 |
| KR | 199008166 | B1 | 11/1990 | WO | WO2005019160 | A1 | 2/2005 |
| KR | 199104132 | B1 | 6/1991 | WO | WO2004042547 | A1 | 5/2005 |
| KR | 199205087 | Y1 | 7/1992 | WO | WO2005042156 | A1 | 5/2005 |
| KR | 2006132885 | A | 12/2006 | WO | WO2005042157 | A2 | 5/2005 |
| MX | 2004PA002764 | A | 6/2004 | WO | WO2005042549 | A1 | 5/2005 |
| NL | 197700262 | A | 7/1977 | WO | WO2005073167 | A1 | 8/2005 |
| NL | 188158 | C | 4/1992 | WO | WO2005073168 | A1 | 8/2005 |
| SU | 677650 | A | 7/1979 | WO | WO2005073169 | A1 | 8/2005 |
| TW | 387874 | B | 4/2000 | WO | WO2005073170 | A1 | 8/2005 |
| TW | 400249 | B | 8/2000 | WO | WO2005073171 | A1 | 8/2005 |
| TW | 453983 | B | 9/2001 | WO | WO2005073172 | A1 | 8/2005 |
| TW | 453985 | B | 9/2001 | WO | WO2005073173 | A1 | 8/2005 |
| TW | 455576 | B | 9/2001 | WO | WO2005073174 | A1 | 8/2005 |
| TW | 457244 | B | 10/2001 | WO | WO2005073175 | A1 | 8/2005 |
| TW | 458959 | B | 10/2001 | WO | WO2005073176 | A1 | 8/2005 |
| TW | 519496 | B | 2/2003 | WO | WO2005073178 | A2 | 8/2005 |
| TW | 527340 | B | 4/2003 | WO | WO2005073179 | A1 | 8/2005 |
| TW | 576837 | B | 2/2004 | WO | WO2005073241 | A1 | 8/2005 |
| TW | 580489 | B | 3/2004 | WO | WO2006040023 | A1 | 4/2006 |
| TW | 580490 | B | 3/2004 | WO | WO2006042675 | A2 | 4/2006 |
| TW | 584623 | B | 4/2004 | WO | WO2005073166 | A3 | 3/2007 |
| TW | 592821 | B | 6/2004 | WO | WO2007051374 | A1 | 5/2007 |
| TW | 226345 | B | 1/2005 | WO | WO2007096274 | A1 | 8/2007 |
| TW | 233438 | B | 6/2005 | | | | |
| TW | 245780 | B | 12/2005 | | | | |
| TW | 266650 | B | 11/2006 | | | | |
| WO | WO7900193 | A1 | 4/1979 | | | | |
| WO | WO9414752 | A1 | 7/1994 | | | | |
| WO | WO9514659 | A1 | 6/1995 | | | | |

| | | | | | | |
|---|---|---|---|---|---|---|
| WO | WO 2007115936 | 10/2007 | | WO | WO 2008008930 A2 | 1/2008 |
| WO | WO2007115936 A2 | 10/2007 | | WO | WO2008028843 A1 | 3/2008 |
| WO | WO2006008928 A2 | 1/2008 | | WO | WO2008062058 A1 | 5/2008 |
| WO | WO2008008926 A2 | 1/2008 | | | | |
| WO | WO2008008929 A2 | 1/2008 | | * cited by examiner | | |

HYDROCYANATION OF 2-PENTENENITRILE

CROSS-REFERENCE TO RELATED APPLICATIONS

This application claims benefit of priority from Provisional Application No. 60/830,864, filed Jul. 14, 2006. This application relates to commonly-assigned application Ser. Nos. 11/776,922, 11/776,932, 11/776,954, and 11/776,968 filed concurrently on Jul. 12, 2007.

FIELD OF THE INVENTION

This invention relates to the hydrocyanation of 2-pentenenitrile to produce adiponitrile and other dinitriles. More particularly, this invention relates to a process for the hydrocyanation of 2-pentenenitrile using a catalyst precursor composition comprising a zero-valent nickel and at least one bidentate phosphite ligand.

BACKGROUND OF THE INVENTION

Hydrocyanation catalyst systems, particularly pertaining to the hydrocyanation of olefins, are well known in the art. For example, systems useful for the hydrocyanation of 1,3-butadiene to form 3-pentenenitrile (3PN) and for the subsequent hydrocyanation of 3PN to form adiponitrile (ADN), are known in the commercially important nylon synthesis field. The hydrocyanation of olefins using transition metal complexes with monodentate phosphite ligand is well documented in the prior art. See, for example, U.S. Pat. Nos. 3,496,215; 3,631,191; 3,655,723 and 3,766,237; and Tolman, C. A., McKinney, R. J., Seidel, W. C., Druliner, J. D., and Stevens, W. R., Advances in Catalysis, Vol. 33, page 1 (1985). Improvements in the zero-valent nickel catalyzed hydrocyanation of ethylenically unsaturated compounds with the use of certain multidentate phosphite ligands are also disclosed. Such improvements are described, for example, in U.S. Pat. Nos. 5,821,378; 5,981,772; 6,020,516; and 6,284,865.

The hydrocyanation of activated olefins such as conjugated olefins (e.g., 1,3-butadiene and styrene) and strained olefins (e.g., norbornene) can proceed at useful rates without the use of a Lewis acid promoter. However the hydrocyanation of unactivated olefins, such as 1-octene and 3PN, requires the use of at least one Lewis acid promoter to obtain industrially useful rates and yields for the production of linear nitriles, such as n-octyl cyanide and adiponitrile, respectively.

The use of a promoter in the hydrocyanation reaction is disclosed, for example, in U.S. Pat. No. 3,496,217. This patent discloses an improvement in hydrocyanation using a promoter selected from a large number of metal cation compounds as nickel catalyst promoters with a wide variety of counterions. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including pentenenitriles (PN), in the presence of a zero-valent nickel catalyst and a triorganotin promoter. Moreover, U.S. Pat. No. 4,874,884 discloses a process for producing ADN by the zero-valent nickel catalyzed hydrocyanation of pentenenitriles in the presence of a synergistic combination of promoters selected in accordance with the desired reaction kinetics of the ADN synthesis. Furthermore, the use of Lewis acids to promote the hydrocyanation of pentenenitriles to produce ADN using zero-valent nickel catalysts with multidentate phosphite ligands is also disclosed. See, for example, U.S. Pat. Nos. 5,512,696; 5,723, 641; 5,959,135; 6,127,567; and 6,646,148.

A recognized shortcoming of the catalyst systems and processes described above is the inability to hydrocyanate the conjugated 2-pentenenitrile isomers, 2PN. U.S. Pat. No. 3,564,040 describes that 3PN is slowly isomerized to 2PN during the hydrocyanation process, and the 2PN so produced is treated as a yield loss. Furthermore, 2PN has been shown to be both a catalyst inhibitor and a catalyst poison as the concentration increases. In order to mitigate this poisoning effect, 2PN is typically separated before recovered pentenenitrile is recycled to the reactor.

In order to address the negative effects of 2PN, U.S. Pat. No. 3,564,040 describes a method to maintain the steady-state concentration of 2PN below 5 mole percent as based on the nitriles present in the reaction mixture. Because trans-2PN is difficult to separate from a mixture of 3PN and 4PN by distillation due to their close relative volatilities, the disclosed method involves the catalytic isomerization of trans-2PN to cis-2PN followed by fractional distillation of the mixture of PN isomers to remove the more volatile cis-2PN isomer. The catalyst systems used to isomerize trans-2PN to cis-2PN are those that also serve to hydrocyanate PN to ADN, in particular, nickel catalysts derived from monodentate phosphite ligands as described in U.S. Pat. Nos. 3,496,217 and 3,496,218.

Alternative catalyst systems for the isomerization of trans-2PN to cis-2PN are disclosed in U.S. Pat. Nos. 3,852,325 and 3,852,327. The primary advantage of the catalyst systems described therein is in avoiding appreciable carbon-carbon double bond migration in the PN isomers, which allows for the isomerization of trans-2PN to cis-2PN without substantial further isomerization of the 3PN to 2PN. The catalysts described in U.S. Pat. No. 3,852,325 are compounds of the general formula $R_3C$—X, such as triphenylmethyl bromide, wherein R is an aryl radical having up to 18 carbon atoms and —X is of the group consisting of —H, —Cl, —Br, —I, —SH, —B($C_6H_5$)$_4$, —P$F_6$, As$F_6$, —Sb$F_6$ and —B$F_4$, while the catalyst systems described in U.S. Pat. No. 3,852,327 are Lewis acid/Lewis base compositions, such as combinations of zinc chloride with triphenylphosphine.

A different method of removing the 2PN from mixtures of PN isomers containing 3PN and 4-pentenenitrile (4PN) is disclosed in U.S. Pat. No. 3,865,865. The 2PN and/or 2-methyl-2-butenenitriles (2M2BN) can be selectively separated from a mixture of PN isomers containing 3PN and 4PN by contacting the mixture of nitriles with an aqueous solution of a treating agent comprising sulfite and bisulfite ions and ammonium or alkali metal cations to produce an aqueous phase containing the bisulfite adduct of the 2PN and/or 2M2BN and an organic phase containing the 3PN and 4PN, substantially free of 2PN or 2M2BN. The recovered organic phase can provide a feed material of PN for further hydrocyanation to produce adiponitrile with greatly reduced amounts of the undesired by-product 2PN that are detrimental to catalyst efficiency.

Recently, a class of hydrocyanation catalysts comprised of zero-valent nickel and a bidentate phosphite ligand have been described that are generally more active than the hydrocyanation catalyst comprised of monodentate phosphites and nickel. As a result, this class of catalysts may be used effectively at much lower concentrations and over a broader range of reaction conditions. U.S. Pat. No. 5,688,986 reveals that at least one member of this class of catalysts are capable of hydrocyanating olefins conjugated to nitriles, for example 2PN. However, we have observed that this ability is not a general feature of this class of catalysts. It therefore would be desirable to identify hydrocyanation catalyst systems that can be resistant to the inhibiting and poisoning effects of 2PN. Also desirable would be processes which use such catalyst systems to produce the valuable products 3PN, 4PN, and/or ADN from 2PN, such as by the isomerization of 2PN to form 3PN and/or 4PN and by the hydrocyanation of 2PN to form ADN.

SUMMARY OF THE INVENTION

In a first aspect, the present invention can provide a process for hydrocyanation, comprising: contacting 2-pentenenitrile with hydrogen cyanide at a temperature in the range of about 0° C. to about 150° C. in the presence of at least one Lewis acid promoter and a catalyst precursor composition, wherein the catalyst precursor composition comprises a zero-valent nickel and at least one bidentate phosphite ligand selected from a member of the group represented by Formula I and Formula II, in which all like reference characters have the same meaning, except as further explicitly limited:

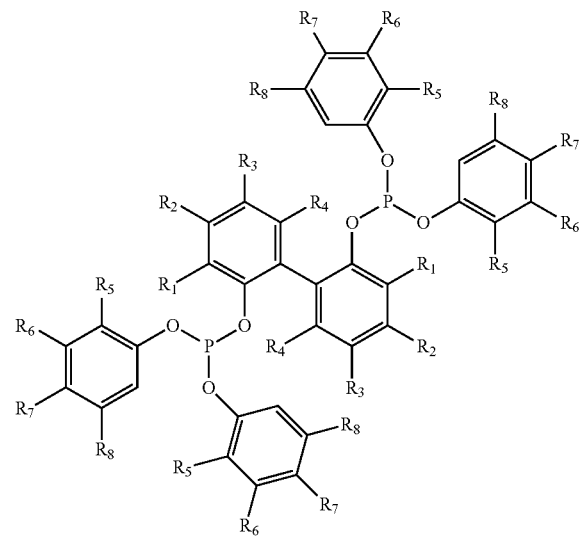

I

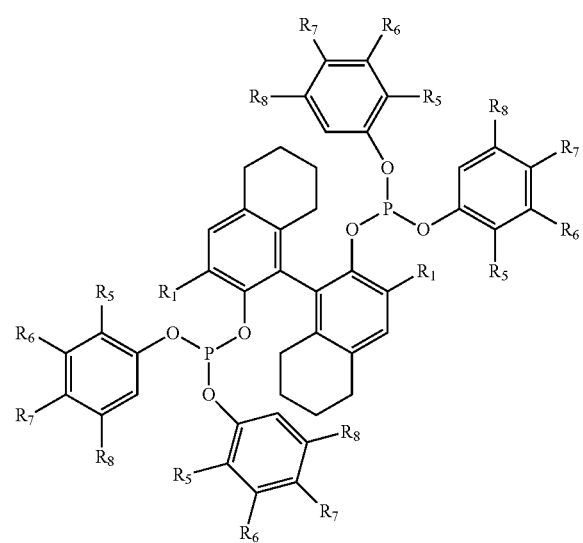

II wherein $R_1$ and $R_5$ are independently selected from the group consisting of $C_1$ to $C_5$ hydrocarbyl; and $R_2$, $R_3$, $R_4$, $R_6$, $R_7$ and $R_8$ are independently selected from the group consisting of H and $C_1$ to $C_4$ hydrocarbyl.

In another aspect, the present invention can provide a process for hydrocyanation as disclosed above, wherein the Lewis acid promoter comprises at least one compound selected from the group consisting of $ZnCl_2$ and $FeCl_2$ or a combination of such members.

In another aspect, the present invention can provide a process for hydrocyanation as disclosed above, wherein the reaction temperature is in the range of about 25° C. to about 80° C.

In another aspect, the present invention can provide a process for hydrocyanation as disclosed above, wherein the molar ratio of the Lewis acid promoter to the nickel present in the reaction ranges from about 1:10 to about 10:1.

In another aspect, the present invention can provide a process for hydrocyanation as disclosed above, where the catalyst precursor composition further comprises at least one monodentate phosphite ligand.

In another aspect, the present invention can provide a process for hydrocyanation as disclosed above, wherein the bidentate phosphite ligand is selected from a member of the group represented by Formula I and Formula II, wherein $R_1$ is methyl, ethyl, isopropyl or cyclopentyl; $R_2$ is H or methyl; $R_3$ is H or a $C_1$ to $C_4$ hydrocarbyl; $R_4$ is H or methyl; $R_5$ is methyl, ethyl or isopropyl; and $R_6$, $R_7$ and $R_8$ are independently selected from the group consisting of H and $C_1$ to $C_4$ hydrocarbyl.

In another aspect, the present invention can provide a process for hydrocyanation as disclosed above, wherein the bidentate phosphite ligand is selected from a member of the group represented by Formula I, wherein $R_1$, $R_4$, and $R_5$ are methyl; $R_2$, $R_6$, $R_7$ and $R_8$ are H; and $R_3$ is $C_1$ to $C_4$ hydrocarbyl.

In another aspect, the present invention can provide a process for hydrocyanation as disclosed above, wherein the bidentate phosphite ligand is selected from a member of the group represented by Formula I, wherein $R_1$ is isopropyl; $R_2$ is H; $R_3$ is $C_1$ to $C_4$ hydrocarbyl; $R_4$ is H or methyl; $R_5$ is methyl or ethyl; $R_6$ and $R_8$, are H or methyl; and $R_7$ is H, methyl or tertiary-butyl.

In another aspect, the present invention can provide a process for hydrocyanation as disclosed above, wherein the bidentate phosphite ligand is selected from a member of the group represented by Formula II, wherein $R_1$ is isopropyl or cyclopentyl; $R_5$ is methyl or isopropyl; and $R_2$, $R_6$, $R_7$, and $R_8$ are H.

In yet another aspect, the present invention can provide a process for producing adiponitrile, comprising: contacting 2-pentenenitrile with hydrogen cyanide at a temperature in the range of about 0° C. to about 150° C. in the presence of at least one Lewis acid promoter and a catalyst precursor composition, wherein the catalyst precursor composition comprises a zero-valent nickel and at least one bidentate phosphite ligand selected from a member of the group represented by Formula I and Formula II, in which all like reference characters have the same meaning, except as further explicitly limited:

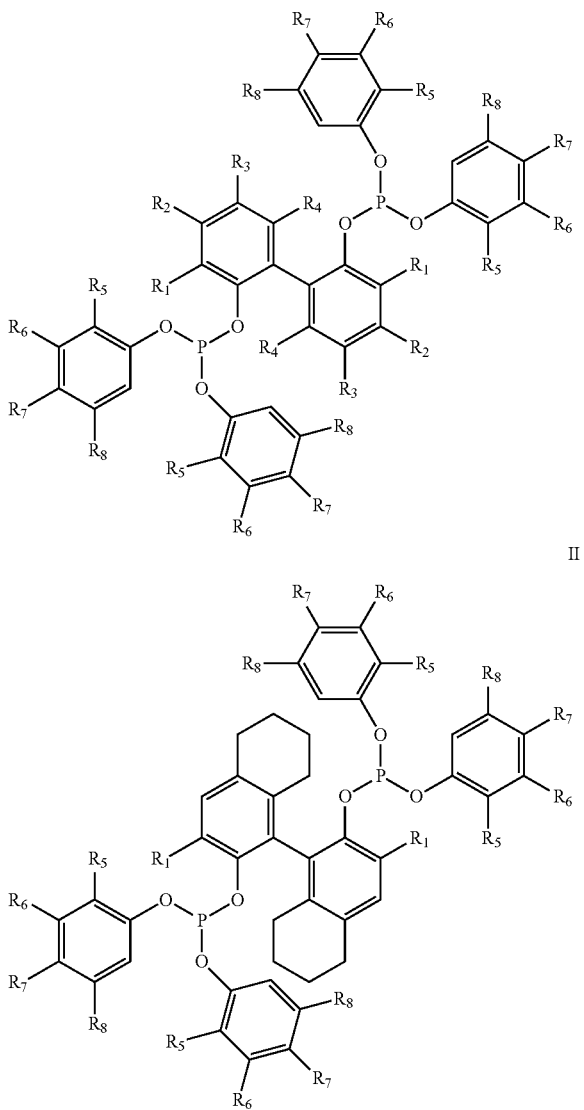

wherein $R_1$ and $R_5$ are independently selected from the group consisting of $C_1$ to $C_5$ hydrocarbyl; and $R_2$, $R_3$, $R_4$, $R_6$, $R_7$ and $R_8$ are independently selected from the group consisting of H and $C_1$ to $C_4$ hydrocarbyl.

In another aspect, the present invention can provide a process for producing adiponitrile as disclosed above, wherein the Lewis acid promoter comprises at least one compound selected from the group consisting of $ZnCl_2$ and $FeCl_2$ or a combination of such members.

In another aspect, the present invention can provide a process for producing adiponitrile as disclosed above, wherein the reaction temperature is in the range of about 25° C. to about 80° C.

In another aspect, the present invention can provide a process for producing adiponitrile as disclosed above, wherein the molar ratio of the Lewis acid promoter to the nickel present in the reaction ranges from about 1:10 to about 10:1.

In another aspect, the present invention can provide a process for producing adiponitrile as disclosed above, wherein the catalyst precursor composition further comprises at least one monodentate phosphite ligand.

In another aspect, the present invention can provide a process for producing adiponitrile as disclosed above, wherein the bidentate phosphite ligand is selected from a member of the group represented by Formula I and Formula II, wherein $R_1$ is methyl, ethyl, isopropyl or cyclopentyl; $R_2$ is H or methyl; $R_3$ is H or a $C_1$ to $C_4$ hydrocarbyl; $R_4$ is H or methyl; $R_5$ is methyl, ethyl or isopropyl; and $R_6$, $R_7$ and $R_8$ are independently selected from the group consisting of H and $C_1$ to $C_4$ hydrocarbyl.

In another aspect, the present invention can provide a process for producing adiponitrile as disclosed above, wherein the bidentate phosphite ligand is selected from a member of the group represented by Formula I, wherein $R_1$, $R_4$, and $R_5$ are methyl; $R_2$, $R_6$, $R_7$ and $R_8$ are H; and $R_3$ is $C_1$ to $C_4$ hydrocarbyl.

In another aspect, the present invention can provide a process for producing adiponitrile as disclosed above, wherein the bidentate phosphite ligand is selected from a member of the group represented by Formula I, wherein $R_1$ is isopropyl; $R_2$ is H; $R_3$ is $C_1$ to $C_4$ hydrocarbyl; $R_4$ is H or methyl; $R_5$ is methyl or ethyl; $R_6$ and $R_8$ are H or methyl; and $R_7$ is H, methyl or tertiary-butyl.

In another aspect, the present invention can provide a process for producing adiponitrile as disclosed above, wherein the bidentate phosphite ligand is selected from a member of the group represented by Formula II, wherein $R_1$ is isopropyl or cyclopentyl; $R_5$ is methyl or isopropyl; and $R_2$, $R_6$, $R_7$, and $R_8$ are H.

DETAILED DESCRIPTION OF THE INVENTION

The invention provides a process for hydrocyanation of 2PN in the presence of at least one Lewis acid and a specified catalyst precursor composition. The 2PN can be present in a mixture of nonconjugated unsaturated nitriles. Additionally, the invention provides a process for producing ADN from 2PN in the presence of at least one Lewis acid and a specified catalyst precursor composition. Furthermore, it has been discovered that the catalyst precursor compositions of the present invention have the ability to alter the ratio of cis- and trans-2PN as well as the ability to isomerize 2PN to 3PN and 4PN in the presence of HCN.

The processes of the invention may comprise the use of a catalyst precursor composition that can resist the inhibiting and poisoning effects of the conjugated pentenenitrile isomer 2PN. The use of the broader class of catalysts, of which these bidentate phosphite ligands and catalyst precursor compositions are a subset, for the hydrocyanation of 3PN has been disclosed in U.S. Pat. Nos. 6,127,567 and 6,171,996.

ADN is of particular interest because it is a commercially versatile and important intermediate in the industrial production of nylon polyamides useful in forming films, fibers, and molded articles.

As used herein, the term "2PN" refers to 2-pentenenitrile and 2-pentenenitriles and includes both cis-2-pentenenitrile (cis-2PN) and trans-2-pentenenitrile (trans-2PN), unless otherwise specified. Similarly, the term "3PN" refers to 3-pentenenitrile and 3-pentenenitriles and includes both cis-3-pentenenitrile (cis-3PN) and trans-3-pentenenitrile (trans-3PN), unless otherwise specified. The term "4PN" refers to 4-pentenenitrile. The term "nonconjugated unsaturated nitriles" means unsaturated nitriles other than 2PN and includes 3PN, 4PN, and nonconjugated methylbutenenitriles. The term "unsaturated nitriles" includes 2PN, 3PN, 4PN, and methylbutenenitriles.

The 2PN useful in the present invention can be prepared by the reaction of hydrogen cyanide with 1,3-butadiene (BD). Using transition metal

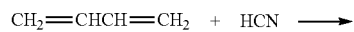
(1)

complexes with monodentate phosphites (for example, U.S. Pat. Nos. 3,496,215; 3,631,191; 3,655,723; and 3,766,237) and zero-valent nickel catalysts with multidentate phosphite ligands (for example, U.S. Pat. Nos. 5,821,378; 5,981,772; 6,020,516; and 6,284,865), the predominant pentenenitrile product formed by the hydrocyanation of BD is trans-3PN. As described in the prior art, the branched BD hydrocyanation product, 2-methyl-3-butenenitrile (2M3BN), can be isomerized to trans-3PN using the same catalyst compositions employed for the hydrocyanation of BD. See, for example, U.S. Pat. Nos. 3,536,748 and 3,676,481. The predominant trans-3PN product from the hydrocyanation of BD and isomerization of 2M3BN also contains smaller quantities of 4PN, cis-3PN, trans-2PN, cis-2PN, and 2-methyl-2-butenenitriles.

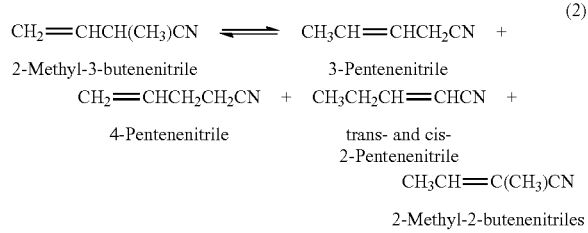
(2)

The 2PN useful in the present invention can be made in larger quantities during the hydrocyanation of 3PN and/or 4PN to form ADN, among other dinitriles, from the concurrent isomerization of 3PN to 2PN, as described in the prior art. Separation of the cis-2PN isomer by the fractional distillation of mixtures of PN isomers, as disclosed in the art, can provide a source of isolated 2PN to be used with the present invention. See, for example, U.S. Pat. No. 3,852,327. 2PN produced by a different process or prepared in a separate manufacturing facility may also be used.

The catalyst precursor composition comprises a zero-valent nickel and at least one bidentate phosphite ligand selected from a member of the group represented by Formula I and Formula II, in which all like reference characters have the same meaning, except as further explicitly limited:

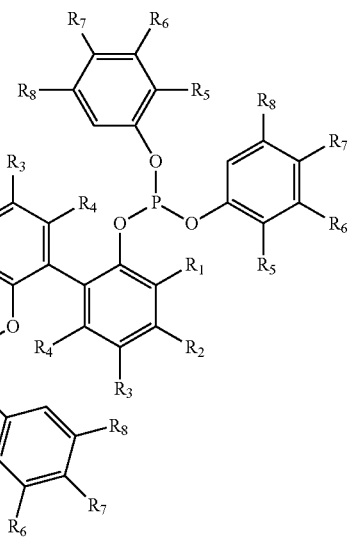

I

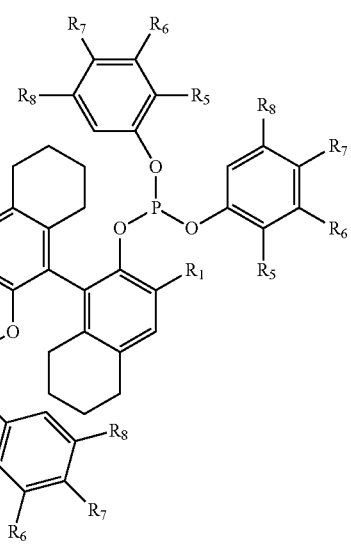

II wherein $R_1$ and $R_5$ are independently selected from the group consisting of $C_1$ to $C_5$ hydrocarbyl, and $R_2, R_3, R_4, R_6, R_7$ and $R_8$ are independently selected from the group consisting of H and $C_1$ to $C_4$ hydrocarbyl.

It will be recognized that Formula I and Formula II are two-dimensional representations of three-dimensional molecules and that rotation about chemical bonds can occur in the molecules to give configurations differing from those shown. For example, rotation about the carbon-carbon bond between the 2- and 2'-positions of the biphenyl and octahydrobinaphthyl bridging groups of Formula I and Formula II, respectively, can bring the two phosphorus atoms of each Formula in closer proximity to one another and can allow the phosphite ligand to bind to a single nickel atom in a bidentate fashion. The term "bidentate" is well known in the art and means both phosphorus atoms of the ligand are bonded to a single nickel atom.

The term "hydrocarbyl" is well known in the art and designates a hydrocarbon molecule from which at least one hydrogen atom has been removed. Such molecules can contain single, double, or triple bonds.

The term "aryl" is well known in the art and designates an aromatic hydrocarbon molecule from which at least one hydrogen atom has been removed.

Examples of suitable aryl groups include those containing 6 to 10 carbon atoms, which can be unsubstituted or singly or multiply substituted. Suitable substituents include, for example, $C_1$-$C_4$ hydrocarbyl, or halogen such as fluorine, chlorine or bromine, or halogenated hydrocarbyl such a trifluoromethyl, or aryl such as phenyl.

Each catalyst precursor composition useful in the present invention may be considered a "precursor" composition in that the zero-valent nickel at some point becomes bound to a bidentate phosphite ligand, and further in all likelihood, additional reactions occur during hydrocyanation, such as, for example, complexing of the initial catalyst composition to an ethylenically unsaturated compound.

As used herein, the term "catalyst precursor composition" also includes within its meaning recycled catalyst, that is, a catalyst precursor composition comprising a zero-valent nickel and at least one bidentate phosphite ligand which, having been used in the process of the invention, is returned or may be returned to the process and used again.

The catalyst precursor compositions may further comprise at least one monodentate phosphite ligand, provided that the monodentate phosphite ligand does not detract from the beneficial aspects of the invention. The monodentate phosphite ligand may be present as an impurity from synthesis of the bidentate phosphite ligand, as disclosed in U.S. Pat. No. 6,069,267, or the monodentate phosphite ligand may be added as an additional component of the catalyst precursor composition.

The catalyst precursor compositions may further comprise at least one Lewis acid promoter.

The bidentate phosphite ligand is selected from a member of the group represented by Formula I and Formula II, in which all like reference characters have the same meaning, except as further explicitly limited:

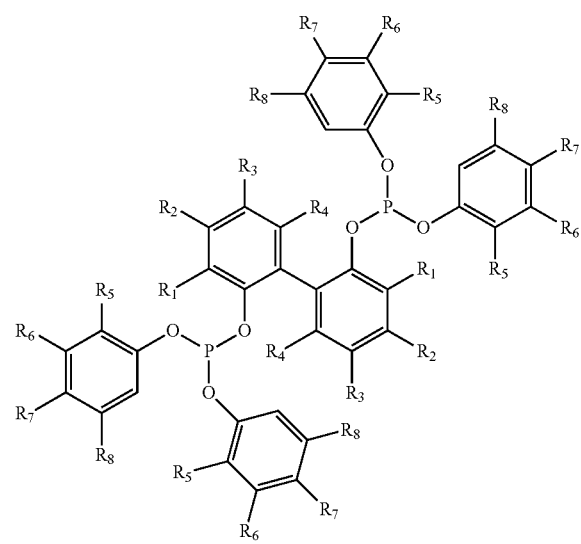

I

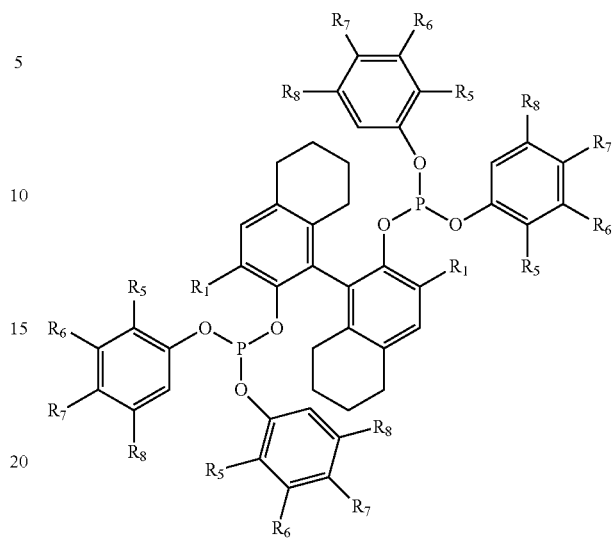

II wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl. For example, the bidentate phosphite ligand can be selected from a member of the group represented by Formula I and Formula II, wherein $R_1$ is methyl, ethyl, isopropyl or cyclopentyl;
$R_2$ is H or methyl;
$R_3$ is H or $C_1$ to $C_4$ hydrocarbyl;
$R_4$ is H or methyl;
$R_5$ is methyl, ethyl or isopropyl; and
$R_6$, $R_7$ and $R_8$ are independently selected from the group consisting of H and $C_1$ to $C_4$ hydrocarbyl.

As additional examples, the bidentate phosphite ligand can be selected from a member of the group represented by Formula I wherein $R_1$, $R_4$ and $R_5$ are methyl; and $R_2$, $R_6$, $R_7$ and $R_8$ are independently selected from the group consisting of H and $R_3$ is $C_1$ to $C_4$ hydrocarbyl. Alternatively, the bidentate phosphite ligand can be selected from a member of the group represented by Formula I wherein $R_1$ is isopropyl; $R_2$ is H; $R_3$ is a $C_1$ to $C_4$ hydrocarbyl; $R_4$ is H or methyl; $R_5$ is methyl or ethyl; $R_6$ and $R_8$ are H or methyl; and $R_7$ is H, methyl or tertiary-butyl; or the bidentate phosphite ligand can be selected from a member of the group represented by Formula II, wherein $R_1$ is isopropyl or cyclopentyl; $R_5$ is methyl or isopropyl; and $R_6$, $R_7$, and $R_8$ are H.

The bidentate phosphite ligands useful in the catalyst precursor compositions employed in the present invention may be prepared by any suitable synthetic means known in the art, for example as described in U.S. Pat. Nos. 6,171,996, 5,512, 696, 6,069,267, and 2004/0106815, all of which are incorporated herein by reference. For example, the reaction of two equivalents of an ortho-substituted phenol with phosphorus trichloride gives the corresponding phosphorochloridite. The reaction of the phosphorochloridite with the desired substituted biphenol or octahydrobinaphthol in the presence of triethylamine gives the bidentate phosphite ligand. The crude bidentate phosphite ligand can be worked up by the process described in U.S. Pat. No. 6,069,267. As disclosed therein, the bidentate phosphite ligand product mixture can typically contain the desired product in about 70% to about 90% selectivity, with other phosphite by-products such as monodentate phosphites making up the balance of the product mixture. The bidentate phosphite ligand itself or these bidentate/monodentate phosphite ligand mixtures are suitable for use with the present invention.

The catalyst precursor compositions employed for this process should ideally be substantially free of carbon monoxide, oxygen, and water and may be preformed or prepared in situ according to techniques well known in the art. The catalyst precursor composition may be formed by contacting the bidentate phosphite ligand with a zero-valent Ni complex having easily displaced ligands. Examples of such zero-valent nickel complexes include $Ni(COD)_2$ (COD is 1,5-cyclooctadiene), $Ni[P(O\text{-}o\text{-}C_6H_4\text{—}CH_3)_3]_3$ and $Ni[P(O\text{-}o\text{-}C_6H_4\text{—}CH_3)_3]_2(C_2H_4)$, all of which are known in the art, wherein 1,5-cyclooctadiene (COD), tris(ortho-tolyl)phosphite $[P(O\text{-}o\text{-}C_6H_4\text{—}CH_3)_3]$, and ethylene $(C_2H_4)$ are the easily displaced ligands. Alternatively, divalent nickel compounds can be combined with a reducing agent, to serve as a source of zero-valent nickel in the reaction, in the presence of the bidentate phosphite ligands of Formula I or Formula II. Suitable divalent nickel compounds include compounds of the formula $NiZ_2$ where Z is halide, carboxylate, or acetylacetonate. Suitable reducing agents include metal borohydrides, metal aluminum hydrides, metal alkyls, Li, Na, K, Zn or $H_2$. See, for example, U.S. Pat. No. 6,893,996. In the catalyst precursor composition, the bidentate phosphite ligand may be present in excess of what can theoretically be coordinated to the nickel at a given time.

The processes of this invention can be carried out in the presence of at least one Lewis acid promoter which affects both the activity and the selectivity of the catalyst system. The promoters exhibit Lewis acidity, as indicated by their ability to coordinate to either a metal-cyanide containing complex or an organonitrile, as measured spectroscopically by a shift in the infrared band assigned to the metal-cyanide or organonitrile stretch upon coordination to the promoter. An example of such a spectroscopically observed shift for a soluble promoter with a nickel-cyanide (Ni—CN) species is described in Advances in Catalysis, Vol. 33 (1985), pages 12-13. The Lewis acid promoters may comprise an inorganic or organometallic compound in which the cation is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin, as is well-known in the art. Examples of Lewis acid promoters include, but are not limited to $BPh_3$, $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_2$, $TiCl_4(THF)_2$, $MnCl_2$, $ScCl_3$, $AlCl_3$, $(C_8H_{17})AlCl_2$, $(C_8H_{17})_2AlCl$, (iso-$C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, $SnCl_2$, $Ph_3Sn(O_3SC_6H_5CH_3)$, and $R_9SnO_3SCF_3$, where $R_9$ is an alkyl or aryl group and Ph is phenyl), or a combination thereof. Preferred promoters include $FeCl_2$ and $ZnCl_2$. The molar ratio of promoter to Ni present in the reaction can, for example, range from about 1:10 to about 10:1.

The catalyst precursor composition may be dissolved in a solvent that is non-reactive toward, and miscible with, the hydrocyanation reaction mixture. Suitable solvents include, for example, aliphatic and aromatic hydrocarbons with 1 to 10 carbon atoms and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign may be used to dissolve the catalyst precursor composition.

The processes of the invention can be carried out with or without a solvent. When carried out with a solvent, the solvent should be liquid at the reaction temperature and pressure, and should be inert towards the 2PN and the catalyst. Examples of such solvents include hydrocarbons such as benzene or xylene, or nitriles such as 3PN, acetonitrile or benzonitrile.

The processes of the invention may typically be carried out at a temperature range from about 0° C. to about 150° C., for example from about 25° C. to about 80° C.

While atmospheric pressure is suitable for carrying out the processes of the invention, higher and lower pressures can be used. In this regard, pressures of from about 0.05 to about 10 atmospheres (about 5.0 to about 1013 kPa) may be used. Higher pressures, up to about 10,000 kPa or more, can be used, if desired, but any benefit that may be obtained thereby may not be justified in view of increased cost of such operations.

The overall feed molar ratio of HCN to zero-valent nickel may, for example, be in the range of about 100:1 to about 3000:1, for example in the range of about 300:1 to about 2000:1. At reactor startup, the reaction vessel may be partially charged, for example, with either a solution of a catalyst precursor composition in substrate pentenenitriles or the reactor product from a previous reaction campaign, followed by initiation of all reactor feeds. Continuous reactor product removal may begin upon establishing the desired fluid levels within the reaction vessel or vessels.

HCN, substantially free of carbon monoxide, oxygen, ammonia, and water can be introduced to the reaction as a vapor, liquid, or mixtures thereof. As an alternative, a cyanohydrin can be used as the source of HCN. See, for example, U.S. Pat. No. 3,655,723.

The reaction medium may be agitated, such as by stirring or shaking. Alternatively, mixing of the reactants and the reaction mixture may be achieved through any means well known in the art that provides mass transfer sufficient to avoid areas of high and/or low reactant concentrations in the reaction mixture. The reaction product and components of the catalyst precursor composition can be recovered by conventional techniques known in the art, such as, for example, by liquid-liquid extraction as disclosed in U.S. Pat. No. 6,936,171, and by distillation. The reaction may be run in batch, semi-continuous, or continuous manner Isomerization of 2PN to 3PN and 4PN in the presence of HCN can be useful in that it can provide the desired 3PN and 4PN isomers, which may be hydrocyanated to form ADN. Additionally, isomerization of 2PN to other PN isomers can be advantageous in that the amount of inhibiting 2PN is reduced. Alteration of the ratio of cis-2PN to trans-2PN can also be advantageous by enabling the purge of cis-2PN from pentenenitrile mixtures. In this way, 2PN can be purged from the 3PN, 4PN, and catalyst mixture which is recycled to the hydrocyanation reactor, and the build-up of 2PN is avoided.

Embodiments falling within the scope of the present invention may be further understood in view of the following non-limiting examples

EXAMPLES

The following procedures can be used to treat cis-2PN before its use in hydrocyanation reactions. Cis-2-pentenenitrile (98%) produced from a 1,3-butadiene and 3PN hydrocyanation process may be obtained commercially from the Sigma-Aldrich Chemical Company. Hydroperoxide impurities can be common in such a reagent and are typically detrimental to hydrocyanation catalyst performance. Hydroperoxide impurities can be measured and reduced in cis-2PN, if necessary, by titration, for example with triphenylphosphine, prior to purification by distillation. Distillation under a nitrogen atmosphere can be utilized to remove the majority of oxygen, water, and peroxides and heavy boilers by taking, for example, a forecut and a heartcut during the distillation. The purified cis-2PN of the heartcut can be transferred into a drybox filled with an inert gas such as nitrogen and can be dried further over 3 A molecular sieves (which have been previously dried and degassed under nitrogen).

The following experimental protocol was used for each of the experiments shown in Table I below.

A $Ni(COD)_2$ (COD=1,5-cyclooctadiene) solution was prepared by dissolving $Ni(COD)_2$ (0.039 g) in toluene (2.79 g). A toluene solution of a ligand of Formula I or Formula II (0.230 mL of 0.21 mol ligand/L of toluene) was treated with $Ni(COD)_2$ solution (0.320 mL) and thoroughly mixed to provide a catalyst precursor solution. A cis-2-pentenenitrile (cis-2PN)/$ZnCl_2$ solution was prepared by dissolving $ZnCl_2$ (0.017 g in 1.02 g cis-2PN). A sample of catalyst solution (0.100 mL) was treated with cis-2PN/$ZnCl_2$ solution (0.025 mL); and the mixture heated to 50° C. From a liquid, uninhibited, anhydrous HCN sample at ambient temperature, HCN vapor was continuously delivered to the reaction mixture over a period of 16 hours. After cooling to ambient temperature, the reaction mixture was treated with acetonitrile (0.125 mL) and analyzed by gas chromatography for the amount of adiponitrile (ADN), 2-methylglutaronitrile (MGN) and 2-ethylsuccinonitrile (ESN) produced. Table I reports the percentage of cis-2PN that was converted to dinitriles (ADN+MGN+ESN). In every case ADN comprised greater than 90% of the dinitriles produced. In the Tables, n-C3H7 is normal-propyl, i-C3H7 is iso-propyl, n-C4H9 is normal-butyl, n-Butyl is normal-butyl, sec-C4H9 is secondary-butyl, and t-C4H9 is tertiary-butyl groups.

TABLE I

| Example | Ligand Formula | R1 | R2 | R3 | R4 | R5 | R6 | R7 | R8 | % c2PN Conversion |
|---|---|---|---|---|---|---|---|---|---|---|
| 1 | I | Me | H | Me | Me | Me | H | H | H | 7 |
| 2 | I | Me | H | Me | Me | Me | H | Me | H | 14 |
| 3 | I | Me | H | Me | Me | Me | H | H | Me | 5 |
| 4 | I | Me | H | Me | Me | Me | H | Me | Me | 5 |
| 5 | I | Me | H | Me | Me | Me | Me | H | H | 2 |
| 6 | I | Me | H | Me | H | Me | H | Me | H | 2 |
| 7 | I | Me | H | Me | Me | C2H5 | H | H | H | 1 |
| 8 | I | Me | H | Me | Me | i-C3H7 | H | H | Me | 0.4 |
| 9 | I | Me | H | Me | Me | n-C3H7 | H | H | H | 0.4 |
| 10 | I | Me | H | Me | Me | i-C3H7 | H | H | H | 0.1 |
| 11 | I | Me | H | i-C3H7 | Me | Me | H | H | H | 0.5 |
| 12 | I | Me | H | n-C4H9 | Me | Me | H | H | H | 20 |
| 13 | I | Me | H | t-C4H9 | Me | Me | H | H | H | 6 |
| 14 | I | Me | H | H | Me | i-C3H7 | H | H | H | 1 |
| 15 | I | Me | H | H | Me | sec-C4H9 | H | H | H | 0.1 |
| 16 | I | Me | Me | Me | Me | Me | H | H | H | 51 |
| 17 | I | C2H5 | H | C2H5 | C2H5 | Me | H | H | H | 0.7 |
| 18 | I | C2H5 | H | t-C4H9 | H | Me | H | H | H | 0.3 |
| 19 | I | i-C3H7 | H | H | H | i-C3H7 | H | H | H | 0.7 |
| 20 | I | i-C3H7 | H | H | Me | Me | H | H | H | 7 |
| 21 | I | i-C3H7 | H | H | Me | Me | H | Me | H | 4 |
| 22 | I | i-C3H7 | H | H | Me | Me | H | H | H | 2 |
| 23 | I | i-C3H7 | H | H | Me | Me | Me | H | H | 1 |
| 24 | I | i-C3H7 | H | H | Me | Me | H | H | Me | 0.4 |
| 25 | I | i-C3H7 | H | Me | H | Me | H | H | H | 6 |
| 26 | I | i-C3H7 | H | Me | H | Me | H | Me | H | 5 |
| 27 | I | i-C3H7 | H | Me | Me | Me | H | H | H | 14 |
| 28 | I | i-C3H7 | H | Me | Me | Me | H | t-C4H9 | H | 43 |
| 29 | I | i-C3H7 | H | Me | Me | Me | H | H | Me | 32 |
| 30 | I | i-C3H7 | H | Me | Me | Me | H | Me | H | 31 |
| 31 | I | i-C3H7 | H | Me | Me | C2H5 | H | H | H | 21 |
| 32 | I | i-C3H7 | H | Me | Me | i-C3H7 | H | H | H | 0.3 |
| 33 | I | i-C3H7 | H | Me | Me | i-C3H7 | H | H | Me | 0.1 |
| 34 | I | i-C3H7 | H | C2H5 | H | Me | H | H | H | 3 |
| 35 | I | i-C3H7 | H | C2H5 | Me | Me | H | H | H | 21 |
| 36 | I | i-C3H7 | H | C2H5 | Me | i-C3H7 | H | H | H | 2 |
| 37 | I | i-C3H7 | H | i-C3H7 | H | Me | H | H | H | 1 |
| 38 | I | i-C3H7 | H | n-C3H7 | Me | Me | H | H | H | 19 |
| 39 | I | i-C3H7 | H | i-C3H7 | Me | Me | H | H | H | 8 |
| 40 | I | i-C3H7 | H | n-C3H7 | Me | i-C3H7 | H | H | H | 1 |
| 41 | I | i-C3H7 | H | t-C4H9 | Me | Me | H | H | H | 5 |
| 42 | I | i-C3H7 | H | t-C4H9 | H | Me | H | H | H | 0.6 |
| 43 | I | cyclopentyl | H | H | Me | n-C3H7 | H | H | H | 0.3 |
| 44 | II | C2H5 | H | — | — | i-C3H7 | H | H | H | 2 |
| 45 | II | i-C3H7 | H | — | — | i-C3H7 | H | H | H | 30 |
| 46 | II | cyclopentyl | H | — | — | Me | H | H | H | 46 |
| 47 | II | cyclopentyl | H | — | — | i-C3H7 | H | H | H | 5 |

Examples 48-69

The following experimental protocol was used for each of the experiments shown in Table II below.

A Ni(COD)$_2$ (COD=1,5-cyclooctadiene) solution was prepared by dissolving Ni(COD)$_2$ in toluene. A toluene solution of a ligand of Formula I or II was treated with the Ni(COD)$_2$ solution and thoroughly mixed to provide a catalyst precursor solution. A cis-2PN/promoter solution was prepared by dissolving the appropriate promoter in cis-2PN. A sample of catalyst solution was treated with the cis-2PN/promoter solution, and the mixture adjusted to the reaction temperature. During the reaction times listed below, HCN vapor was continuously delivered to the 2PN catalyst solution from a liquid, uninhibited, anhydrous HCN sample at ambient temperature.

For Examples 58-60, the molar ratio of Ni to cis-2PN was 1 to 67. The molar ratio of promoter to Ni was 3 to 1. The molar ratio of ligand to Ni was 3 to 1. The reaction was carried out at 25° C. for 72 hours.

For Examples 61-64, the molar ratio of Ni to cis-2PN was 1 to 67. The molar ratio of promoter to Ni was 3 to 1. The molar ratio of ligand to Ni was 3 to 1. The reaction was carried out at 25° C. for 72 hours.

For Example 65, the molar ratio of Ni to cis-2PN was 1 to 200. The molar ratio of promoter to Ni was 1 to 1. The molar ratio of ligand to Ni was 2 to 1. The reaction was carried out at 50° C. for 6 hours.

For Examples 66-69, the molar ratio of Ni to cis-2PN was 1 to 67. The molar ratio of promoter to Ni was 3 to 1. The molar ratio of ligand to Ni was 3 to 1. The reaction was carried out at 25° C. for 72 hours.

TABLE II

| Example | Ligand Formula | R1 | R2 | R3 | R4 | R5 | R6 | R7 | R8 | Promoter | % cis-2PN Conversion |
|---|---|---|---|---|---|---|---|---|---|---|---|
| 48 | I | i-C3H7 | H | Me | Me | Me | H | H | H | ZnBr$_2$ | 13.0 |
| 49 | I | i-C3H7 | H | Me | Me | Me | H | H | H | FeBr$_2$ | 18.4 |
| 50 | I | i-C3H7 | H | Me | Me | Me | H | H | H | CoCl$_2$ | 10.2 |
| 51 | I | i-C3H7 | H | Me | Me | Me | H | H | H | FeCl$_2$ | 17.1 |
| 52 | I | i-C3H7 | H | Me | Me | Me | H | H | H | FeCl$_2$ | 45.0 |
| 53 | I | i-C3H7 | H | Me | Me | Me | H | Me | H | FeCl$_2$ | 51.4 |
| 54 | I | i-C3H7 | H | Me | Me | Me | Me | H | H | FeCl$_2$ | 40.2 |
| 55 | I | i-C3H7 | H | Me | Me | Me | H | t-C4H9 | H | FeCl$_2$ | 59.6 |
| 56 | I | i-C3H7 | H | Me | Me | Me | H | t-C4H9 | H | LaCl$_3$ | 3.0 |
| 57 | I | i-C3H7 | H | Me | H | Me | H | H | H | FeCl$_2$ | 9.0 |
| 58 | I | Me | H | Me | Me | Me | H | H | H | FeCl$_2$ | 6.5 |
| 59 | I | i-C3H7 | H | i-C3H7 | Me | Me | H | H | H | FeCl$_2$ | 8.1 |
| 60 | I | i-C3H7 | H | Me | H | Me | H | Me | H | FeCl$_2$ | 4.8 |
| 61 | II | Ethyl | H | — | — | i-C3H7 | H | H | H | FeCl$_2$ | 2.2 |
| 62 | I | i-C3H7 | H | Ethyl | Me | Me | H | H | H | FeCl$_2$ | 20.6 |
| 63 | I | i-C3H7 | H | Ethyl | Me | i-C3H7 | H | H | H | FeCl$_2$ | 2.1 |
| 64 | II | i-C3H7 | H | — | — | Me | H | H | H | FeCl$_2$ | 29.7 |
| 65 | I | Me | Me | Me | Me | Me | H | H | H | FeCl$_2$ | 37.8 |
| 66 | I | Me | H | n-Butyl | Me | Me | H | H | H | FeCl$_2$ | 20.1 |
| 67 | II | Cyclopentyl | H | — | — | Me | H | H | H | FeCl$_2$ | 29.2 |
| 68 | II | Cyclopentyl | H | — | — | i-C3H7 | H | H | H | FeCl$_2$ | 4.2 |
| 69 | I | i-C3H7 | H | Me | Me | Et | H | H | H | FeCl$_2$ | 13.2 |

The specified temperature was maintained during the reaction period. After the reaction was terminated, the mixture was treated with acetonitrile and analyzed by gas chromatography for the amount of adiponitrile (ADN), 2-methylglutaronitrile (MGN) and 2-ethylsuccinonitrile (ESN) produced. Table II reports the percentage of cis-2PN that was converted to dinitriles (ADN+MGN+ESN). In every case, ADN comprised greater than 90% of the dinitriles produced.

For Examples 48-51, the molar ratio of Ni to cis-2PN was 1 to 200. The molar ratio of promoter to Ni was 3 to 1. The molar ratio of ligand to Ni was 3 to 1. The reaction was carried out at 25° C. for 95 hours.

For Examples 52-55, the molar ratio of Ni to cis-2PN was 1 to 67. The molar ratio of promoter to Ni was 1 to 1. The molar ratio of ligand to Ni was 3 to 1. The reaction was carried out at 50° C. for 6 hours.

For Example 56 the molar ratio of Ni to cis-2PN was 1 to 67. The molar ratio of promoter to Ni was 3 to 1. The molar ratio of ligand to Ni was 3 to 1. The reaction was carried out at 25° C. for 70 hours.

For Example 57, the molar ratio of Ni to cis-2PN was 1 to 200. The molar ratio of promoter to Ni was 1 to 1. The molar ratio of ligand to Ni was 2 to 1. The reaction was carried out at 50° C. for 70 hours.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for producing adiponitrile, comprising:
    contacting 2-pentenenitrile with hydrogen cyanide at a temperature in the range of about 0° C. to about 150° C. in the presence of at least one Lewis acid promoter and a catalyst precursor composition, wherein the catalyst precursor composition comprises a zero-valent nickel and at least one bidentate phosphite ligand selected from a member of the group represented by Formula I and Formula II, in which all like reference characters have the same meaning, except as further explicitly limited:

I

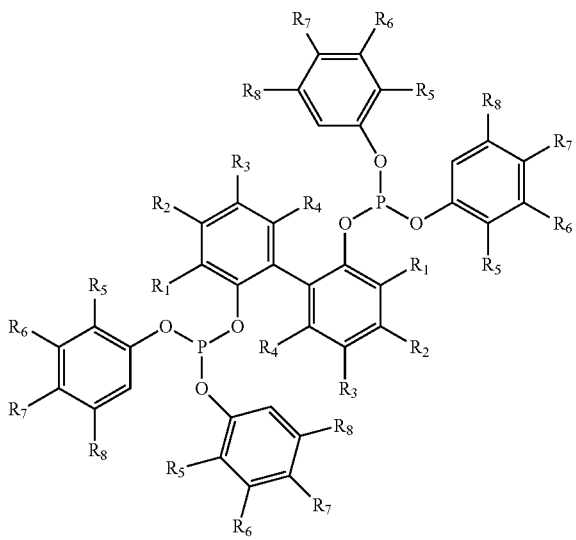

II

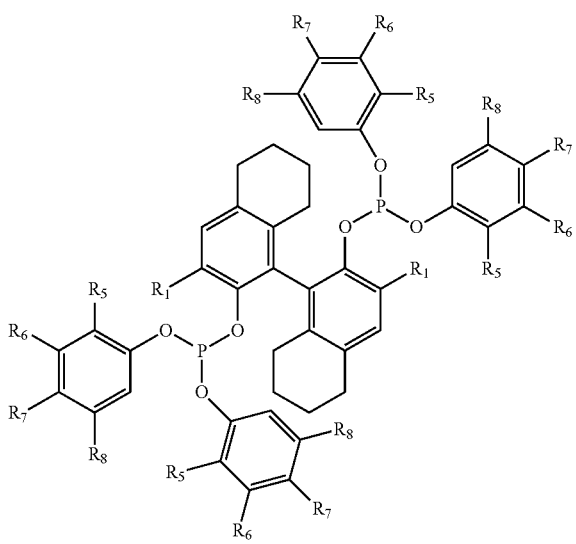

wherein $R_1$ and $R_5$ are independently selected from the group consisting of $C_1$ to $C_5$ hydrocarbyl; and $R_2$, $R_3$, $R_4$, $R_6$, $R_7$ and $R_8$ are independently selected from the group consisting of H and $C_1$ to $C_4$ hydrocarbyl.

2. The process of claim 1, wherein the bidentate phosphite ligand is selected from a member of the group represented by Formula I and Formula II, wherein $R_1$ is methyl, ethyl, isopropyl or cyclopentyl;

$R_2$ is H or methyl;

$R_3$ is H or a $C_1$ to $C_4$ hydrocarbyl;

$R_4$ is H or methyl;

$R_5$ is methyl, ethyl or isopropyl; and $R_6$, $R_7$ and $R_8$ are independently selected from the group consisting of H and $C_1$ to $C_4$ hydrocarbyl.

3. The process of claim 1, wherein the bidentate phosphite ligand is selected from a member of the group represented by Formula I, wherein $R_1$ is isopropyl; $R_2$ is H; $R_3$ is $C_1$ to $C_4$ hydrocarbyl; $R_4$ is H or methyl; $R_5$ is methyl or ethyl; $R_6$ and $R_8$ are H or methyl; and $R_7$ is H, methyl or tertiary-butyl.

4. The process of claim 1, wherein the bidentate phosphite ligand is selected from a member of the group represented by Formula II, wherein $R_1$ is isopropyl or cyclopentyl; $R_5$ is methyl or isopropyl; and $R_2$, $R_6$, $R_7$, and $R_8$ are H.

5. The process of claim 1, wherein the Lewis acid promoter comprises at least one compound selected from the group consisting of $ZnCl_2$ and $FeCl_2$ or a combination of such members.

6. The process of claim 1, wherein the reaction temperature is between about 25° C. and about 80° C.

7. The process of claim 1, wherein the molar ratio of the Lewis acid promoter to Ni present in the reaction ranges from about 1:10 to about 10:1.

8. The process of claim 1, wherein the catalyst precursor composition further comprises at least one monodentate phosphite ligand.

\* \* \* \* \*